(12) United States Patent
Herrwerth et al.

(10) Patent No.: US 8,138,372 B2
(45) Date of Patent: Mar. 20, 2012

(54) ZWITTERIONIC COMPOUNDS AND USE THEREOF

(75) Inventors: Sascha Herrwerth, Essen (DE); Hans Henning Wenk, Mulheim a. d. Ruhr (DE); Burghard Gruning, Essen (DE); Petra Allef, Krefeld (DE); Uwe Begoihn, Essen (DE)

(73) Assignee: Evonik Goldschmidt GmbH, Essen (DE)

( * ) Notice: Subject to any disclaimer, the term of this patent is extended or adjusted under 35 U.S.C. 154(b) by 816 days.

(21) Appl. No.: 12/138,097

(22) Filed: Jun. 12, 2008

(65) Prior Publication Data

US 2009/0054521 A1 Feb. 26, 2009

(30) Foreign Application Priority Data

Aug. 23, 2007 (DE) .......................... 10 2007 040 000

(51) Int. Cl.
*C07C 229/04* (2006.01)
*A61K 31/205* (2006.01)

(52) U.S. Cl. ........................................ 562/561; 514/556
(58) Field of Classification Search .................. 562/561; 514/556

See application file for complete search history.

(56) References Cited

U.S. PATENT DOCUMENTS

| | | | |
|---|---|---|---|
| 4,988,806 A | 1/1991 | Gruning et al. | |
| 5,023,246 A | 6/1991 | Gruning et al. | |
| 5,124,446 A | 6/1992 | Gruning et al. | |
| 5,354,906 A | 10/1994 | Weitemeyer et al. | |
| 5,470,992 A | 11/1995 | Gruning et al. | |
| 5,491,245 A | 2/1996 | Gruning et al. | |
| 5,645,842 A | 7/1997 | Gruning et al. | |
| 5,792,737 A | 8/1998 | Gruning et al. | |
| 7,163,916 B2 | 1/2007 | Allef et al. | |
| 7,297,675 B2 | 11/2007 | Allef et al. | |
| 2004/0258651 A1 | 12/2004 | Pascaly et al. | |
| 2005/0232877 A1 | 10/2005 | Schunicht et al. | |
| 2006/0188456 A1 | 8/2006 | Ferenz et al. | |
| 2007/0231289 A1 | 10/2007 | Gruning et al. | |
| 2008/0027202 A1 | 1/2008 | Ferenz et al. | |
| 2008/0108709 A1 | 5/2008 | Meyer et al. | |

FOREIGN PATENT DOCUMENTS

| | | | |
|---|---|---|---|
| EP | 0 418 697 | * | 3/1991 |
| EP | 0656346 A1 | | 6/1995 |
| FR | 2 604 622 | * | 4/1988 |
| JP | 62275250 | | 11/1987 |
| JP | 6-80987 | * | 3/1994 |
| JP | 6228070 | | 8/1994 |
| WO | WO9701528 | | 1/1997 |

OTHER PUBLICATIONS

Thomson Scientific, Database WPI Week 199437, London, GB; AN 1994-299740.
Thomson Scientific, Database WPI Week 198802, London, GB, AN 1988-011516.
U.S. Appl. No. 12/134,703, filed Jun. 6, 2008, entitled "Cosmetic and Pharmaceutical Oil-In-Water Emulsions Containing an Ester Quat," First Named Inventor: Anna Howe.
Grüning, B., et al., "Parfümerie und Kosmetik," 1996, pp. 244-248, 77(4).

* cited by examiner

*Primary Examiner* — Shailendra Kumar
(74) *Attorney, Agent, or Firm* — Scully, Scott, Murphy & Presser, P.C.

(57) ABSTRACT

The present invention covers zwitterionic, non-surface-active compounds in the form of carboxymethylated, short-chain dialkylaminoalkylamides and use thereof as therapeutic agent.

9 Claims, 4 Drawing Sheets

ZWITTERIONIC COMPOUNDS AND USE THEREOF

FIELD OF THE INVENTION

The present invention relates to zwitterionic compounds and their preparation, which can be obtained by carboxyalkylation of a short-chain dialkylaminoalkylamide.

BACKGROUND OF THE INVENTION

Glycinate compounds, as are obtained by carboxymethylation of the dimethylaminopropylamides of fatty acids, have been known for a long time. Such compounds which are known under the name "amidopropylbetaines" are typically used as surfactants (see e.g., Parfümerie und Kosmetik, 1996, 77(4), 244-248).

Known compounds of this substance class are derived, for example, from coconut fatty acids, hydrogenated coconut fatty acids or coconut fatty acid fractions (e.g., cocoamidopropylbetaine). They are used widely, e.g., as secondary surfactants in cosmetic preparations (e.g., shower gels, shampoos, liquid soaps) and in dishwashing detergents.

A characteristic feature of prior art amidopropylbetaines is their surface-active behaviour, i.e., the property to reduce the surface tension of aqueous systems. This property is caused by the molecular structure, namely by the hydrophobic, long-chain fatty acid radical on one hand, and the hydrophilic, zwitterionic dimethylammonium glycinate group on the other hand. The current fatty acid radicals comprise, in particular, those which occur in natural fats. More particularly, the fatty acid radicals of amidopropylbetaines include coconut fat or hydrogenated coconut fat, namely saturated and unsaturated $C_8$-$C_{18}$ fatty acids. Amidopropylbetaines of caproic acid (C6) have also been described.

Many zwitterionic substances, such as, for example, amine oxides, proline, ectoin or trimethylglycine are so-called cosmotropes, i.e., they increase the structure or order of aqueous systems. Many of these substances are known to be osmolytes, i.e., they control the water content of cells and thus have a stabilizing effect.

A disadvantageous effect of many surfactants is the irritation of skin and eyes. Although the irritation potential of the amidopropyldimethyl glycinates is lower than, for example, that of the alkyl sulphates or alkyl ether sulphates, the amidopropyldimethyl glycinates are, however, not completely free from possible irritative effects.

As such, there is a need to provide compounds which, despite having the zwitterionic, hydrophilic head group, do not have a cell-damaging effect like surfactants according to the prior art. That is, compounds are needed that contain a zwitterionic, hydrophilic head group, yet have no surface-active structures and thus preferably do not irritate skin and eyes. There is also a need to prepare these zwitterionic compounds using processes which permit large-scale industrial production.

SUMMARY OF THE INVENTION

Surprisingly, it has been found that, in contrast to prior art amidopropyldimethyl glycinates based on long-chain fatty acids such as described above, the compounds according to the invention which contain a zwitterionic, hydrophilic head group do not have a cell-damaging effect and are non-irritative, which presumably can be attributed to the lack of surface-active properties.

Particularly surprisingly, it has been found that compounds according to the invention bring about an anti-inflammatory effect in skin models.

Specifically, the present invention provides compounds of the general formula I

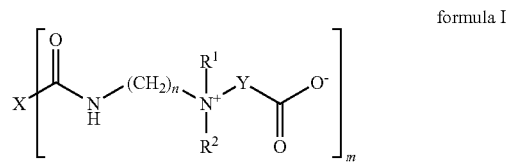

formula I where n=1 to 6, m=1 to 4, $R^1$ and $R^2$, independently of one another, are identical or different, aliphatic hydrocarbon radicals having 1 to 6 carbon atoms, Y is a divalent hydrocarbon radical, and X is an m-valent radical or a covalent bond, where X, when m=1, is an H, ethyl, hydroxymethyl, 1-hydroxyethyl, 2-hydroxyethyl, 1-hydroxypropyl, 2-hydroxypropyl or 3-hydroxypropyl, and X, when m=2, is a direct covalent bond or a 2-valent $C_1$- to $C_5$-hydrocarbon radical that is unsubstituted or substituted by at least one OH group and X, when m>2, is an m-valent $C_1$- to $C_5$-hydrocarbon radical that is unsubstituted or substituted by at least one OH group.

A further advantage of the compounds according to the invention is their low molecular weight compared with conventionally used compounds, as a result of which it is possible to achieve a higher concentration of ionic and/or zwitterionic structures.

In one embodiment of the present invention, the inventive compounds described above can be used as therapeutic active ingredients.

In another embodiment of the invention, the compounds described above can be used for the treatment of dermatological disorders.

In yet another embodiment of the invention, the inventive compounds can be used for the treatment of inflammatory skin disorders.

In addition to the above, the present invention also provides a process for the preparation of the inventive compounds described above. The process of the invention includes first reacting a carboxylic acid according to formula II

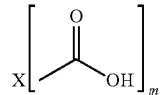

formula II with an amine of the formula III

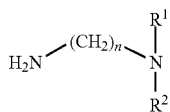

formula III under conditions to give an amidoamine according to formula IV

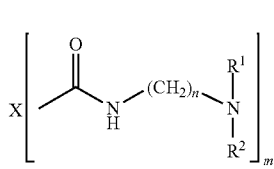

formula IV where
n=1 to 6,
m=1 to 4,
$R^1$ and $R^2$, independently of one another, are identical or different, aliphatic hydrocarbon radicals having 1 to 6 carbon atoms, and
X is an m-valent radical or a covalent bond, where
  X, when m=1, is an H, ethyl, hydroxymethyl, 1-hydroxyethyl, 2-hydroxyethyl, 1-hydroxypropyl, 2-hydroxypropyl or 3-hydroxypropyl and
  X, when m=2, is a direct bond or a 2-valent $C_1$- to $C_5$-hydrocarbon radical that is unsubstituted or substituted by at least one OH group, and
  X, when m>2, is an m-valent $C_1$- to $C_5$-hydrocarbon radical that is unsubstituted or substituted by at least one OH group.

The inventive process further includes reacting the amidoamine of formula IV obtained in the first reacting step with an ω-halocarboxylic acid or its salt which has an acid radical according to formula V

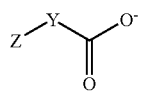

formula V to give the compound of the formula I
where
Z=a halogen, and
Y is a divalent hydrocarbon radical.

One advantage of the process according to the invention consists in the possibility of preparing the compounds according to the invention in high concentrations without gel formation and thus without viscosity problems.

DETAILED DESCRIPTION OF THE INVENTION

Figure 1:
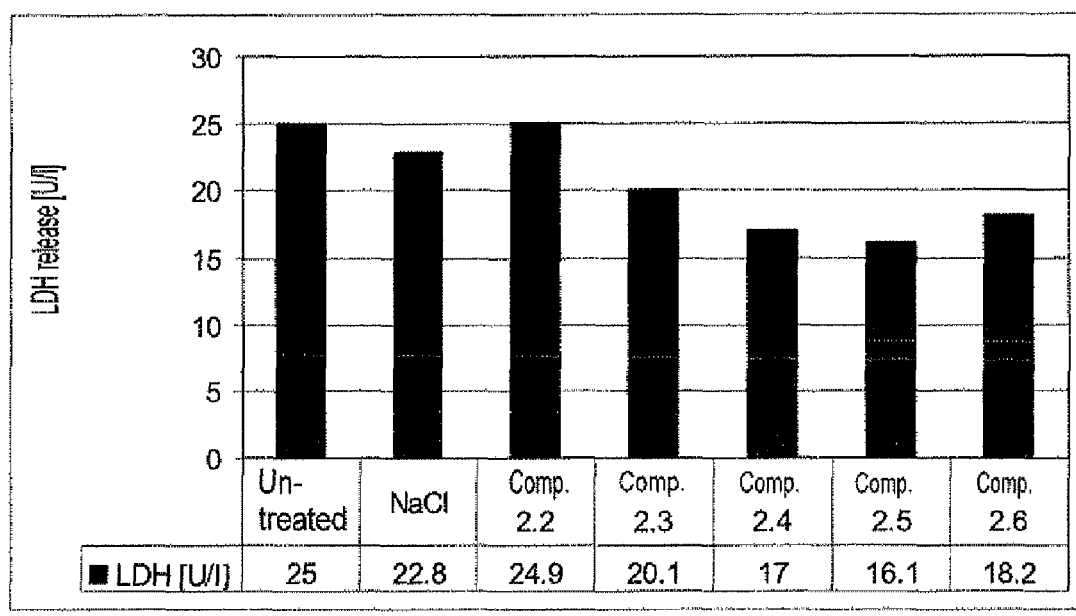
FIG. 1 is a graph illustrating the lactate dehydrogenase (LDH) release 24 hours after the last application of various formulations as described in Example 3.1.

The compounds according to the invention and the process for the preparation of such compounds are described below by way of example, but are not intended to restrict the invention to these exemplary embodiments. Where ranges, general formulae or compound classes are stated below, then these are intended to include not only the corresponding ranges or groups of compounds that are explicitly mentioned, but also all part ranges and part groups of compounds which can be obtained by removing individual values (ranges) or compounds. Where documents are cited in the course of the present description, then their content should, in its entirety, form part of the disclosure content of the present invention.

"Short-chain", zwitterionic, non-surface-active compounds are to be understood below as meaning those which according to formula I have an X with ≦5 carbon atoms.

"Relatively long-chain or long-chain" zwitterionic, non-surface-active compounds are to be understood as meaning those which have an X with >5 carbon atoms.

Unless stated otherwise, all of the percentages quoted (%) are percentages by mass.

The present invention covers compounds of the general formula I

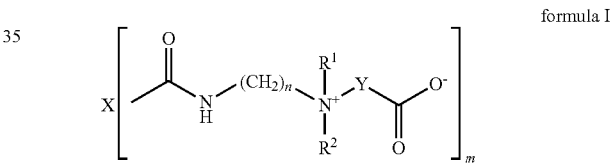

formula I where
n=1 to 6, preferably 1 to 3, preferably 3, and m=1 to 4, preferably 1 or 2, and $R^1$ and $R^2$, independently of one another, are identical or different, aliphatic hydrocarbon radicals having 1 to 6 carbon atoms, preferably $C_1$- to $C_3$-hydrocarbon radicals and preferably $CH_3$ radicals, and Y is a divalent hydrocarbon radical, preferably —$CH_2$—, and X is an m-valent radical or a covalent bond, where: when m=1, X=H, ethyl, hydroxymethyl, 1-hydroxyethyl, 2-hydroxyethyl, 1-hydroxypropyl, 2-hydroxypropyl or 3-hydroxypropyl and when m=2, X=direct bond, —$CH_2$—, —CH(OS)—, —$CH_2$CH(OH)— or —CH(OH)CH(OH)— and X when m=2 is a direct bond or a 2-valent $C_1$- to $C_5$-hydrocarbon radical that is unsubstituted or substituted by at least one OH group, and X when m>2 is an m-valent $C_1$- to $C_5$-hydrocarbon radical that is unsubstituted or substituted by at least one OH group.

In a preferred embodiment of the compounds of formula I according to the invention, m=2 and X is a direct covalent bond, $CH_2$, CH(OH), $CH_2$CH(OH) or CH(O(H)CH(OH), preferably X=$CH_2$. A particularly preferred compound of the invention is the embodiment of formula I in which n=3, m=2, $R^1$=$R^2$=$CH_3$, Y=$CH_2$ and X=$CH_2$.

In a further preferred embodiment of the compounds of formula I according to the invention, m=1 and X=H. A particularly preferred compound is the embodiment of formula I in which n=3, m=1, $R^1=R^2=CH_3$, $Y=CH_2$, and X=H.

The invention further provides a medicament consisting of an active amount of at least one of the compounds according to the invention, and the use of the compounds according to the invention as a medicament.

As shown in Examples 3.1 to 3.4, compounds according to the invention have both a cell-protective effect and also an anti-inflammatory effect on reconstituted human epidermis. Compounds according to the invention for use as therapeutic active ingredients are thus provided by the invention.

Since the cell-protecting and antiapoptotic effect can be demonstrated particularly well on skin cells, a preferred use of the compounds according to the invention is one for the treatment of dermatological disorders, particularly for the treatment of inflammatory skin disorders.

By way of example, mention may be made here of: psoriasis vulgaris, pyoderma gangraenosum, subcorneal pustulose Sneddon Wilkinson, atopic dermatitis, granuloma anulare, pemphigus vulgaris, vitiligo, atopic eczema, psoriasis, neurodermatitis, urticaria, vasculitis allergica, allergic alveolitis, contact eczema, seborrhoeic eczema, dishidrotic eczema, medicinal eczema, general allergic skin disorders, alopecia greata, alopecia totalis, alopecia subtotalis, alopecia universalis, alopecia diffusa, lupus erythematodes of the skin, lichen planus, dermatomyostis of the skin, morphea, sclerodermy, psoriasis capitis, psoriasis guttata, psoriasis inversa, alopecia greata ophiasis type, androgenetic alopecia, allergic contact eczema, irritative contact eczema, contact eczema, pemphigus foliaceus, pemphigus vegetans, cicatricial mucosa pemphigoid, bulbous pemphigoid, mucosa pemphigoid, dermatitis, dermatitis herpetiformis duhring, necrobiosis lipoidica, erythema nodosum, lichen vidal, prurigo simplex, prurigo nodularis, pmmigo acuta, linear IgA dermatosis, polymorphous photodermatosis, erythema solaris, lichen sclerosus, erioral dennatitis, exanthema of the skin, medicinal exanthema, purpura chronica progressiva, dihidrotic eczema, eczema, fixed medicinal exanthema, photoallergic skin reaction, lichen simplex or graft versus host disease.

The medicament according to the invention can be administered by any administration route known to one skilled in the art, such as, for example, intranasally, intravenously, intramuscularly, topically and locally, preference being given to topical and local administration in the case of skin disorders. Therapy of the skin disorders can take place in a conventional manner, e.g., by means of bandages, plasters, compresses, reconstitutable lyophilizates, as plasters or paste or gels which comprise the compounds according to the invention, although the compounds according to the invention can also be administered in the form of liposome complexes or gold particle complexes topically and locally in the region of the diseased skin area. Further topical administrations can take place, for example, in the form of a solution, an emulsion, a cream, an ointment, a foam, an aerosol spray, a gel matrix, a sponge as reconstitutable lyophilizate, as plaster or as paste, drops or washes.

The compounds according to formula I according to the invention can be prepared, for example, using the process according to the invention described below.

This process is characterized in that in a first process step, i.e., Step A, a carboxylic acid according to formula II

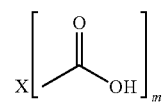

formula II is reacted with an amine of formula III:

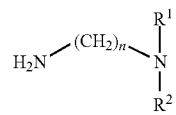

formula III to give an amidoamine according to formula IV:

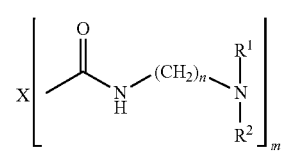

formula IV where n=1 to 6 and m=1 to 4, and $R^1$ and $R^2$, independently of one another, are identical or different, aliphatic hydrocarbon radicals having 1 to 6 carbon atoms, and X is an m-valent radical or a covalent bond, where, when m=1, X=H, ethyl, hydroxymethyl, 1-hydroxyethyl, 2-hydroxyethyl, 1-hydroxypropyl, 2-hydroxypropyl or 3-hydroxypropyl, and, when m=2, X=direct bond, —$CH_2$—, —CH(OH)—, —$CH_2$CH(OH)— or —CH(OH)CH(OH)— and X, when m=2, is a direct bond or a 2-valent $C_1$- to $C_5$-hydrocarbon radical that is unsubstituted or substituted by at least one OH group, and X, when in >2, is an m-valent $C_1$- to $C_5$-hydrocarbon radical that is unsubstituted or substituted by at least one OH group. Next, and in a second process step, i.e., Step B, the amidoamine of the formula IV obtained in A is reacted with an ω-halocarboxylic acid or its salt, preferably metal salt, in particular sodium salt, which has an acid radical according to formula V

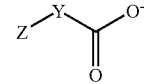

formula V to give the compound of formula I, where Z a halogen and Y is a divalent hydrocarbon radical.

Carboxylic acids that can be used in process Step A are all mono-, di- or polycarboxylic acids or else mixtures of these which satisfy the conditions specified for formula II. For preparing a dizwitterionic compound of formula I where m=2, the carboxylic acids used in process Step A are preferably oxalic acid (HOOC—COOH), tartronic acid (HOOC—$CH_2$(OH)—COOH), malic acid (HOOC—$CH_2$(OH)—$CH_2$—COOH) and tartaric acid (HOOC—$CH_2$(OH)—$CH_2$(OH)—COOH), particularly preferably malonic acid (HOOC—$CH_2$—COOH). Preferred carboxylic acids in Step A for preparing the substance according to the invention according to formula I with preferred m=1 are lactic acid, propionic acid and glycolic acid, particularly preferably formic acid (HCOOH).

The amine component that can be used is any suitable amine compound which satisfies the conditions of formula III. Preferably, 3-(diethylamino)propylamine, 2-(diethylamino)ethylamine or 2-(dimethylamino)ethylamine are used. A particularly preferred amine component is dimethylaminopropylamine (DMAPA).

Preferably, in Step A of the process according to the invention, an acid component according to formula II is reacted with an amine component according to formula III at a temperature of from 90° C. to 220° C., particularly preferably at a temperature of about 180° C., to give an amidoamine according to formula IV. Step A of the process according to the invention is particularly preferably carried out using a suitable catalyst. The suitable catalysts used are preferably strong base catalysts, such as, for example, alkoxides, particularly preferably sodium ethoxide, potassium ethoxide, sodium methoxide and potassium methoxide.

The water that forms in the reaction can be removed from the product. The water is preferably distilled off under the reaction conditions and thus removed from the product mixture. Particularly at temperatures below about 130° C., it is advantageous to apply a sub-atmospheric pressure in order to increase the rate of water removal through distillation.

The reaction scheme below shows one possible reaction course of process Step A.

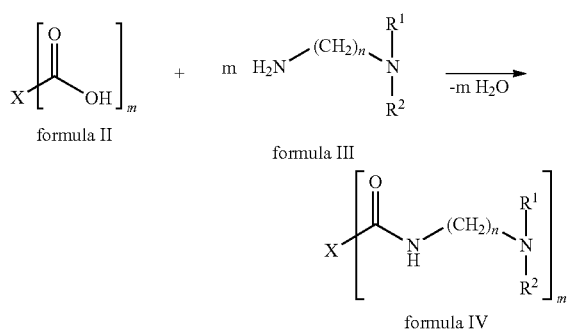

formula II     formula III formula IV

Since the salt mixtures that form in Step A of the inventive process are solid at the start of the reaction, the acid component according to formula II in the process according to the invention is preferably added to the initially introduced amine component according to formula III, in reverse order compared with the prior art.

In the production of short-chain amidoamines according to formula IV, the greatly increased exothermy, compared to amidoamines of longer-chain fatty acids known from the prior art, during salt formation between amine according to formula III and acid according to formula II should be taken into consideration which is caused by the low molecular weights and consequently higher quantitative amount concentrations. In this regard, and in a preferred embodiment of the process according to the invention, process parameters specifically adapted in process Step A can be used such that the addition of the carboxylic acid component to the amine component takes place so slowly that the temperature of the reaction mixture does not exceed 130° C., preferably 100° C., during the addition. At higher temperatures, larger amounts of the amine component could be driven out by the water that forms, which can have negative consequences on the stoichiometry of the components used. To maintain the specified temperature ranges, counter-cooling is preferably carried out in order to achieve an economically useful metering rate.

Step B of the inventive process can take place in the presence of a suitable solvent in an amount which ensures the stirrability and pumpability of the reaction mixture at any time point in the process. Preferably, the reaction takes place in the presence of water as solvent. Step B of the inventive process is preferably carried out at a temperature of about 70-10° C. The halide Z that is prepared as by-product can be removed from the reaction solution or remain in it. If the halide is to be removed, then, for example, precipitation with a suitable solvent or dialysis can be used. A preferred solvent for the precipitation is ethanol.

In preferred embodiments of the process according to the invention, the halide Z remains in the solution.

Monohalocarboxylic acids or monohalocarboxylic acid salt with an acid radical according to formula V that can be used are all halocarboxylic acids whose acid radical satisfies the conditions specified for formula V. A particularly preferred monohalocarboxylic acid salt according to formula V is the monochloroacetate.

As already in Step A of the inventive process, the greatly increased exothermy, compared to the processes of the prior art and caused by the low molar mass of the short-chain amidoamine component, should also be taken into consideration in process Step B. Therefore, in Step B of the process according to the invention, the reaction preferably takes place such that, during and after complete addition of the halocarboxylic acid component to the amidoamine component until the heat of reaction has subsided, the reaction temperature is kept at a maximum of about 70° C., with counter-cooling if necessary. The subsequent reaction preferably takes place a little below the boiling point of the solvent where, when using water as solvent, temperatures in the range from 95-99° C. are preferably used.

The reaction scheme below shows one possible reaction course of Step B of the inventive process.

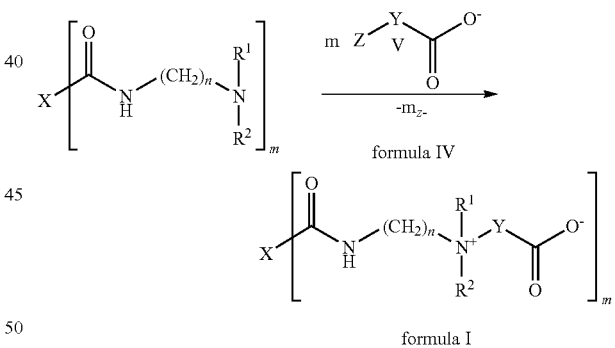

formula IV formula I

The reaction of amidoamines according to formula IV to give the corresponding compounds according to formula I takes place as described preferably in a solvent. The amidoamines are preferably used in concentrations of from 3 to 75%, preferably 5 to 50%. The solution of compounds according to formula I that forms in this process step can be used with, or without, further concentration or desalting steps, e.g., for preparing cosmetic preparations. In a further preferred embodiment of the process according to the invention, the compound of formula I according to the invention is desalted by precipitation of the halide component with a suitable solvent or by dialysis, or concentrated by distillation of all or part of the solvent. Preferably, the solutions that form after Step B of the inventive process are used without further work-up steps.

In preferred embodiments of the process according to the invention, the amine II used in excess in process Step A is removed prior to the reaction with the halocarboxylic acid component in process Step B. This can take place, for example, by distillation at reduced pressure.

In the examples listed below, the present invention is described by way of example without any intention to restrict the invention, the scope of application of which arises from the entire description and the claims, to the embodiments specified in the examples.

EXAMPLES

Example 1.1

Preparation of Compound 1.1

In a 500 ml stirred apparatus with reflux condenser and nitrogen inlet, 100 g of formic acid were initially introduced and rendered inert with nitrogen for about 10 minutes. Then, 225 ml of 3-dimethylaminopropylamine were added with stirring and continuing inertization with nitrogen. The salt formation was exothermic and the mixture heated up to about 175° C. and was held at this temperature for about 4-5 h. During this time, water forming in the reaction was removed from the mixture via a column. If, by reference to the acid number, a degree of conversion of about 98% was reached, excess DMAPA was removed by means of vacuum distillation. The content of tertiary nitrogen in the purified end product was 10.4%.

Example 1.2

Preparation of Compound 1.2

In a 500 ml stirred apparatus with reflux condenser and nitrogen inlet, 133 g of lactic acid were initially introduced and rendered inert with nitrogen for about 10 minutes. Then, 188 ml of 3-dimethylaminopropylamine were added with stirring and continuing inertization with nitrogen. The salt formation was exothermic and the mixture heated up to about 150° C. and was held at a temperature of 175° C. for about 4-5 h. During this time, water forming during the reaction was removed from the mixture via a column. If, by reference to the acid number, a degree of conversion of about 98% was reached, excess DMAPA was removed by means of vacuum distillation. The content of tertiary nitrogen in the purified end product was 8.14%.

Example 1.3

Preparation of Compound 1.3

In a 500 ml stirred apparatus with reflux condenser and nitrogen inlet, 148 g of propionic acid were initially introduced and rendered inert with nitrogen for about 10 minutes. Then, 280 ml of 3-dimethylaminopropylamine were added with stirring and continuing inertization with nitrogen. The salt formation was exothermic and the mixture heated up to about 150° C. and was held at a temperature of 175° C. for about 4-5 h. During this time, water forming during the reaction was removed from the mixture via a column. If, by reference to the acid number, a degree of conversion of about 98% was reached, excess DMAPA was removed by means of vacuum distillation. The content of tertiary nitrogen in the purified end product was 8.91%.

Example 1.4

Preparation of Compound 1.4

90 g of oxalic acid were initially introduced into a 500 ml stirred apparatus with reflux condenser and nitrogen inlet. Then, 328 ml of 3-dimethylaminopropylamine were added with stirring and continuing inertization with nitrogen. After the melting of the resulting solid, the salt formation was exothermic and the mixture heated up to about 150° C. and was held at a temperature of 175° C. under nitrogen for about 4-5 h. During this time, water forming during the reaction was removed from the mixture via a column. If, by reference to the acid number, a degree of conversion of about 98% was reached, excess DMAPA was removed by means of vacuum distillation. The content of tertiary nitrogen in the purified end product was 12.5%.

Example 1.5

Preparation of Compound 1.5

104 g of malonic acid were initially introduced into a 500 ml stirred apparatus with reflux condenser and nitrogen inlet. Then, 280 ml of 3-dimethylaminopropylamine were added with stirring and continuous inertization with nitrogen. After the melting of the resulting solid, the salt formation was exothermic and the mixture heated up to about 140° C. and was held at a temperature of 175° C. under nitrogen for about 4-5 h. During this time, water forming during the reaction was removed from the mixture via a column. If, by reference to the acid number, a degree of conversion of about 98% was reached, excess DMAPA was removed by means of vacuum distillation. The content of tertiary nitrogen in the purified end product was 9.84%.

Example 1.6

Preparation of Compound 1.6

76 g of glycolic acid were initially introduced into a 500 ml stirred apparatus with reflux condenser and nitrogen inlet. Then, 135 ml of 3-dimethyaminopropylamine were added with stirring and continuous inertization with nitrogen. After the melting of the resulting solid, the salt formation was exothermic and the mixture heated up to about 140° C. and was held at a temperature of 175° C. under nitrogen for about 4-5 h. During this time, water forming during the reaction was removed from the mixture via a column. If, by reference to the acid number, a degree of conversion of about 98% was reached, excess DMAPA was removed by means of vacuum distillation. The content of tertiary nitrogen in the purified end product was 8.96%.

Example 2.1

Preparation of Compound 2.1

In a 500 ml four-neck flask equipped with stirrer, thermometer, reflux condenser and dropping funnel, 91 g of Na monochloroacetate and 191 g of water were weighed in and heated to 40° C. 100 g of the amidoamine from Example 1.1 were added and the reaction mixture was held at a temperature of 70° C. until the heat of reaction had subsided. The mixture was then heated to 98° C. After about 7 h, the content of residual amidoamine was below 0.5%.

382 g of an aqueous solution of the following composition were obtained:

| | |
|---|---|
| Compound 2.1: | 38.1% |
| NaCl: | 11.9% |
| Water: | 50% |
| Appearance: | liquid, clear |

Example 2.2

Preparation of Compound 2.2

In a 500 ml four-neck flask equipped with stirrer, thermometer, reflux condenser and dropping funnel, 70 g of Na monochloroacetate and 170 g of water were weighed in and heated to 40° C. 100 g of the amidoamine from Example 1.2 were added. The reaction mixture was then heated to 70° C. and the temperature held until the heat of reaction had subsided. The mixture was then heated to 98° C. After about 7 h, the content of residual amidoamine was below 0.5%.

340 g of an aqueous solution of the following composition were obtained:

| | |
|---|---|
| Compound 2.2: | 39.7% |
| NaCl: | 10.3% |
| Water: | 50% |
| Appearance: | liquid, clear |

Example 2.3

Preparation of Compound 2.3

In a 1000 ml four-neck flask equipped with stirrer, thermometer, reflux condenser and dropping funnel, 153 g of Na monochloroacetate and 353 g of water were weighed in and heated to 40° C. 200 g of the amidoamine from Example 1.3 were added. The reaction mixture was then heated to 70° C. and the temperature maintained until the heat of reaction had subsided. The mixture was then heated to 98° C. After about 7 h, the content of residual amidoamine was below 0.5%.

706 g of an aqueous solution of the following composition were obtained:

| | |
|---|---|
| Compound 2.3: | 39.2% |
| NaCl: | 10.8% |
| Water: | 50% |
| Appearance: | liquid, clear |

Example 2.4

Preparation of Compound 2.4

In a 500 ml four-neck flask equipped with stirrer, thermometer, reflux condenser and dropping funnel, 107 g of Na monochloroacetate and 207 g of water were weighed in and heated to 40° C. 100 g of the amidoamine from Example 1.4 were added. The reaction mixture was then heated to 70° C. and the temperature held until the heat of reaction had subsided. The mixture was then heated to 98° C. After about 7 h, the content of residual amidoamine was below 0.5%.

414 g of an aqueous solution of the following composition were obtained:

| | |
|---|---|
| Compound 2.4: | 35.9% |
| NaCl: | 14.1% |
| Water: | 50% |
| Appearance: | liquid, clear |

Example 2.5

Preparation of Compound 2.5

In a 500 ml four-neck flask equipped with stirrer, thermometer, reflux condenser and dropping funnel, 85 g of Na monochloroacetate and 185 g of water were weighed in and heated to 40° C. 100 g of the amidoamine from Example 1.5 were added. The reaction mixture was then heated to 70° C. and the temperature held until the heat of reaction had subsided. The mixture was then heated to 98° C. After about 7 h, the content of residual amidoamine was below 0.5%.

370 g of an aqueous solution of the following composition were obtained:

| | |
|---|---|
| Compound 2.5: | 38.5% |
| NaCl: | 11.5% |
| Water: | 50% |
| Appearance: | liquid, clear |

Example 2.6

Preparation of Compound 2.6

In a 1000 ml four-neck flask equipped with stirrer, thermometer, reflux condenser and dropping funnel, 115 g of Na monochloroacetate and 265 g of water were weighed in and heated to 40° C. 150 g of the amidoamine from Example 1.6 were added. The reaction mixture was then heated to 70° C. and the temperature held until the heat of reaction had subsided. The mixture was then heated to 98° C. After about 7 h, the content of residual amidoamine was below 0.5%.

530 g of an aqueous solution of the following composition were obtained:

| | |
|---|---|
| Compound 2.6: | 38.5% |
| NaCl: | 11.5% |
| Water: | 50% |
| Appearance: | liquid, clear |

Effectivity Examples for Compounds According to the Invention

In order to be able to characterize the therapeutic and skincare properties of Compounds 2.1 to 2.6, various in vitro tests were carried out on skin models (reconstituted human epidermis, company: SkinEthic).

Example 3.1

Lactate Dehydrogenase Release

LDH Release

The occurrence of LDH in the cell culture medium is a sure sign of damage to the cytoplasmatic membrane of the cells and thus damage of the epidermal cell layer. Furthermore, it is known that an outflow of this enzyme represents the "point of no return" for the cell, i.e., indicates an irreversibility of the damage.

The LDH concentration was determined using a commercially available test kit (LDH test kit, Roche Diagnostics, Mannheim, Germany).

The test formulation was applied to the skin models twice with an interval of 24 h.

FIG. 1 shows the LDH release 24 h after the last application.

Test formulation 3.1: A 4% strength aqueous solution of the compounds according to the invention was applied. Since the zwitterionic, non-surface-active compounds comprise about 0.3% of sodium chloride per 1% of active substance, the corresponding sodium chloride concentration was additionally tested.

As a result of the application of the zwitterionic compounds, the LDH release from the cells was unchanged or even slightly lower compared to the untreated skin model. This means that the compounds according to the invention do not attack the cell membrane and do not have a cell-damaging effect but, very much so on the contrary, even assist these cells and their proliferation.

Example 3.2

LDH Release Following Damage to the Cells with SDS

Sodium dodecyl sulphate (SDS) is known to attack the cell membrane and lead to increased LDH release. Using the experiment described below, the aim was to investigate to what extent Compound 2.1 can protect the cells following damage with SDS.

The skin models were damaged with SDS for 40 min. The test formulation, an O/W cream with 1 or 4% of Compound 2.1, was then applied. The LDH release was measured 24 and 48 h after application of the test formulation.

Test Formulation 3.2:

| Polyglyceryl-3 methylglucose distearate | 3.0% |
|---|---|
| Glyceryl stearate | 2.0% |
| Stearyl alcohol | 1.0% |
| Cetearyl ethylhexanoate | 5.0% |
| Mineral oil | 14.0% |
| Compound 2.1 | 1.0/4.0% |
| Water | ad 100.0% |

Figure 2:
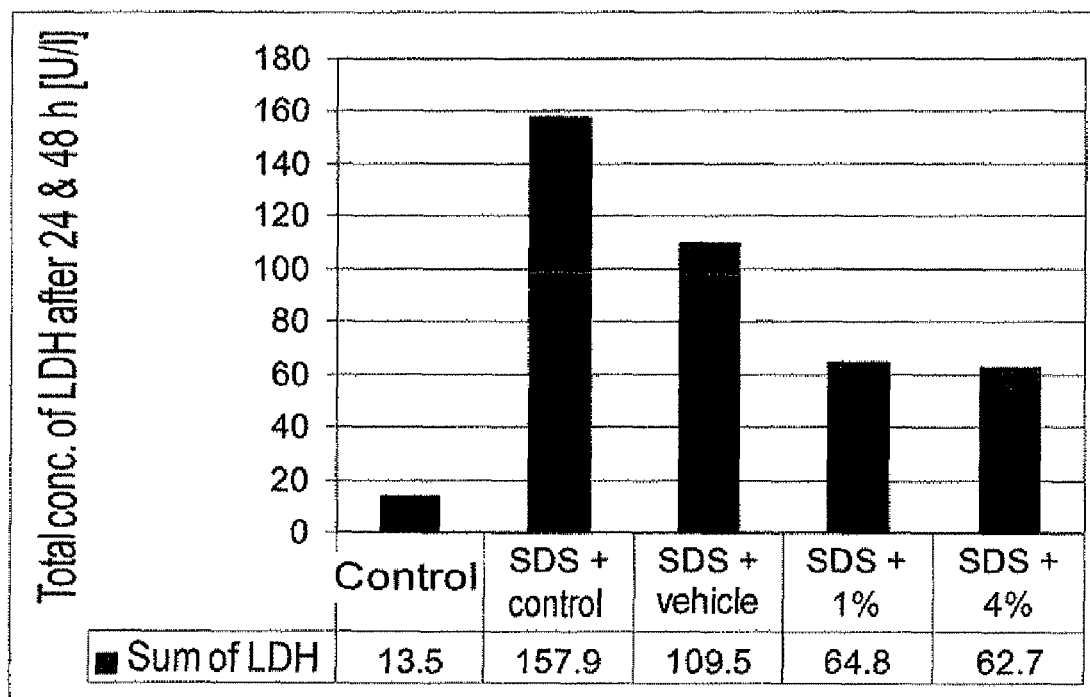
FIG. 2 is a graph illustrating the total concentration of LDH after 24 and 48 hours of application of various formulations as described in Example 3.2.

FIG. 2 shows the total concentration of LDH after 24 and 48 h.

As a result of the damage with SDS, the LDH release increased greatly, as expected. This increase was significantly reduced when the test formulation was applied directly after damage. A positive effect was evident even in the case of the vehicle, but increased significantly again when the formulation comprised Compound 2.1. In this connection, just 1% of the compound according to the invention appears to be adequate since with 4% no significant increase in the effectiveness was evident.

Example 3.3

Il-1α Release Following Damage with SDS

IL1-α is a messenger which plays a central role in inflammatory reactions in the body. Sodium lauryl sulphate (SDS) is a skin-irritative surfactant which can cause an irritative contact dermatitis in people, is used as model irritative in subject studies and, inter alia, induces the release of IL-1α. The IL-1α concentration was determined using a commercially available test kit (human IL-1α immunoassay, R&D Systems GmbH, Wiesbaden, Germany).

The test formulation, a 4% strength aqueous solution of the short-chain, zwitterionic compounds, was applied to the skin models 24 h after the application, 0.25% strength SDS solution was used to create damage for 40 min. The test formulation was then applied a second time. After an incubation time of a further 24 h, the released cytokine IL-1α was determined.

Since the test solutions comprise about 0.3% of NaCl per 1% of active substance, an appropriately concentrated sodium chloride solution was also analysed.

Figure 3:
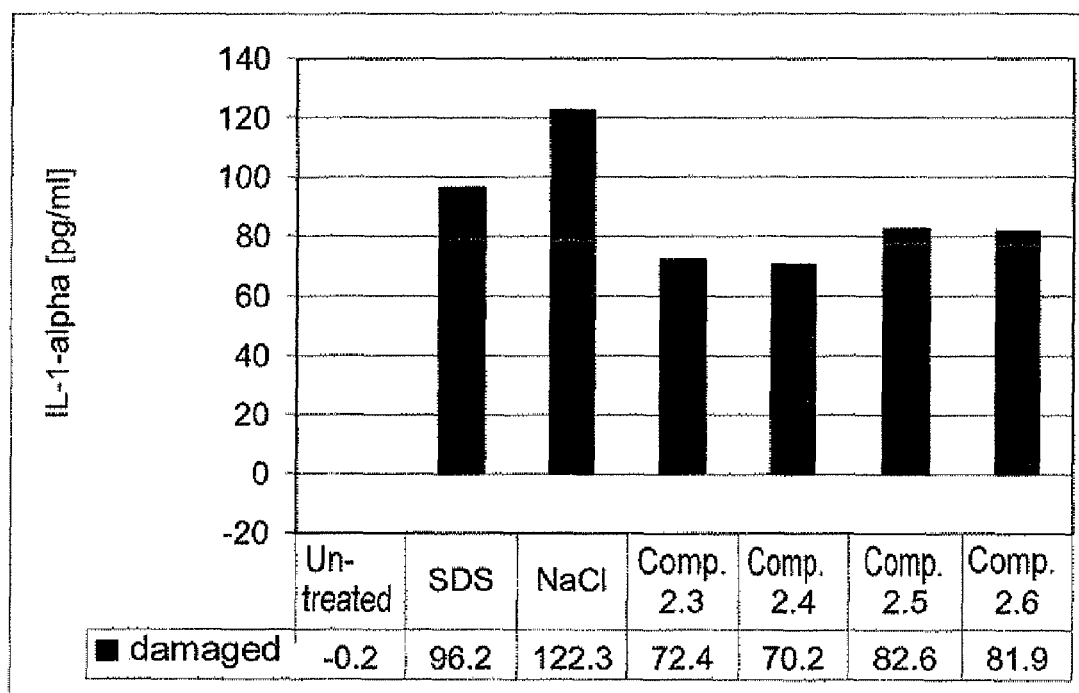
FIG. 3 is a graph illustrating the measurement values of the IL-1α concentration after damage as described in Example 3.3.

FIG. 3 shows the measurement values of the IL-1α concentration 24 h after damage.

All of the tested zwitterionic, non-surface-active compounds reduced the release of the inflammation marker Il-1α, i.e., it can be assumed that the short-chain, zwitterionic compounds have anti-inflammatory properties.

Example 3.4

Anti-Inflammatory Effect of an O/W Cream Containing Compound 2.1

The aim was to investigate whether the anti-inflammatory effect of the compounds according to the invention is also present upon application from a cosmetic formulation. For this purpose, skin models were damaged with SDS. The test formulation was then applied. 24 and 48 h after the application, the Il-1α concentration was determined.

Test Formulation:

| Polyglyceryl-3 methylglucose distearate | 3.0% |
|---|---|
| Glyceryl stearate | 2.0% |
| Stearyl alcohol | 1.0% |
| Cetearyl ethylhexanoate | 5.0% |
| Mineral oil | 14.0% |
| Compound 2.1 | 1.0/4.0% |
| Water | ad 100.0% |

Figure 4:
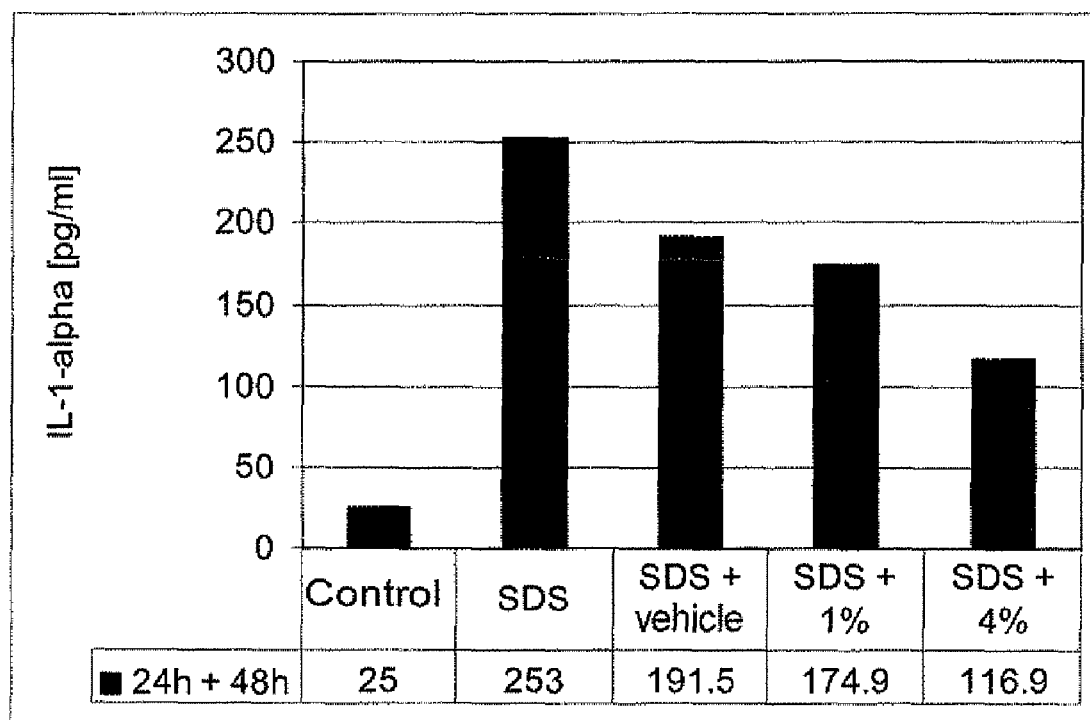
FIG. 4 is a graph illustrating the summed IL-1α concentration after 24 and 48 hours as described in Example 3.4.

FIG. 4 shows the summed IL-1α concentration after 24 and 48 h.

As expected, as a result of the damage with SDS, the formation of the cytokine IL-1α increased greatly. This increase was reduced to a relatively high degree depending on the concentration by adding Compound 2.1, meaning that also upon application of the compounds according to the invention from an O/W emulsion, a marked anti-inflammatory effect is evident.

While the present invention has been particularly shown and described with respect to preferred embodiments thereof it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A compound of general formula I

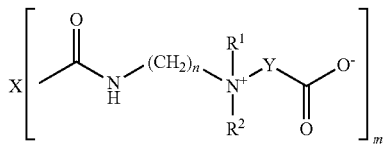

formula I where
n=1 to 6,
m=1,
R¹ and R², independently of one another, are identical or different, aliphatic hydrocarbon radicals having 1 to 6 carbon atoms,
Y is a divalent hydrocarbon radical, and
X is hydrogen.

2. The compound according to claim 1, wherein n=3.

3. The compound according to claim 1, wherein $R^1=R^2=CH_3$.

4. The compound according to claim 1, wherein $Y=CH_2$.

5. The compound according to claim 1, wherein n=3, $R^1=R^2=CH_3$, and $Y=CH_2$.

6. A therapeutic active ingredient including a compound of claim 1.

7. A method for the treatment of dermatological disorders comprising administering a compound of claim 1 to a human including at least one dermatological disorder.

8. A method for the treatment of inflammatory skin disorders comprising administering a compound of claim 1 to a human including at least one inflammatory disorder.

9. A process for the preparation of a compound of general formula I

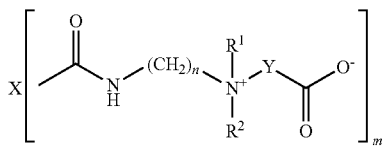

formula I where
n=1 to 6,
m=1,
R¹ and R², independently of one another, are identical or different, aliphatic hydrocarbon radicals having 1 to 6 carbon atoms,
Y is a divalent hydrocarbon radical, and
X is hydrogen,
said process comprising:
reacting, in a first reaction step, a carboxylic acid according to formula II

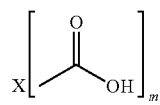

formula II with an amine of formula III

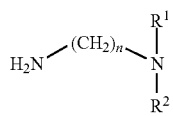

formula III to produce an amidoamine according to formula IV

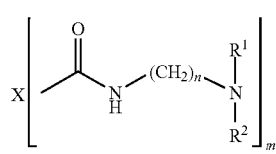

formula IV where
n=1 to 6,
m=1,
R¹ and R², independently of one another, are identical or different, aliphatic hydrocarbon radicals having 1 to 6 carbon atoms, and
X is hydrogen;
and
reacting, in a second reaction step, the amidoamine of formula IV obtained in the first reaction step with an ω-halocarboxylic acid or its salt which has an acid radical according to formula V

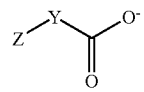

formula V to give the compound of the formula I
where
Z=a halogen, and
Y is a divalent hydrocarbon radical.

* * * * *